United States Patent
Leveson et al.

(10) Patent No.: US 7,935,840 B2
(45) Date of Patent: May 3, 2011

(54) METHOD FOR CONTINUOUS PRODUCTION OF BIODIESEL FUEL

(75) Inventors: Philip D. Leveson, Hannawa Falls, NY (US); John Paul Gaus, Watertown, NY (US)

(73) Assignee: Nextgen Fuel, Inc., Potsdam, NY (US)

( * ) Notice: Subject to any disclaimer, the term of this patent is extended or adjusted under 35 U.S.C. 154(b) by 1052 days.

(21) Appl. No.: 11/676,888

(22) Filed: Feb. 20, 2007

(65) Prior Publication Data

US 2007/0196250 A1    Aug. 23, 2007

Related U.S. Application Data

(60) Provisional application No. 60/775,409, filed on Feb. 21, 2006.

(51) Int. Cl.
*C11C 3/00* (2006.01)
(52) U.S. Cl. ........................................... 554/170
(58) Field of Classification Search ............... 554/170
See application file for complete search history.

(56) References Cited

U.S. PATENT DOCUMENTS

| | | | |
|---|---|---|---|
| 5,908,946 | A | 6/1999 | Stern et al. |
| 6,015,440 | A | 1/2000 | Noureddini |
| 6,364,917 | B1 | 4/2002 | Matsumura et al. |
| 6,712,867 | B1 | 3/2004 | Boocock |
| 2003/0175182 | A1 | 9/2003 | Teall et al. |
| 2003/0229238 | A1* | 12/2003 | Fleisher ............... 554/174 |
| 2006/0021277 | A1 | 2/2006 | Petersen et al. |

OTHER PUBLICATIONS

Gerper et al. Biodiesel Production Technology, Aug. 2002-Jan. 2004.*

* cited by examiner

*Primary Examiner* — Deborah D Carr
(74) *Attorney, Agent, or Firm* — Cantor Colburn LLP

(57) ABSTRACT

An apparatus and method for the continuous production of biofuel by the transesterification of a triglyceride. The apparatus comprises a high shear homogenizer; a reaction chamber; a gravity driven separation device; an evacuated packed thin film stripper; a counter current pack water contactor; and, an evacuated packed spray drier, wherein each component operates with minimal heat and mass transfer resulting in a high capacity process with a reduced footprint.

6 Claims, 2 Drawing Sheets

METHOD FOR CONTINUOUS PRODUCTION OF BIODIESEL FUEL

CROSS-REFERENCE TO RELATED APPLICATION

This application claims benefit of U.S. provisional patent application No. 60/775,409, filed Feb. 21, 2006, entitled CONTINUOUS PRODUCTION OF BIODIESEL FUEL and commonly assigned to the assignee of the present application, the disclosure of which is incorporated by reference in its entirety herein.

FIELD OF THE INVENTION

This invention relates to an intensified process and apparatus for the continuous transesterification of a triglyceride.

BACKGROUND OF THE INVENTION

Many processes within the chemical industry suffer from heat and mass limitations. These limitations result in increased processing times, reduced plant capacity, excessive product inventory and may even result in reduced yields. A relatively new design strategy, named Process Intensification (PI), has been developed in order that these process limitations can be minimized. The resulting processes are often smaller, more efficient, safer, lighter and all so importantly cheaper than the original process. The strategy can deliver these improvements by utilizing unit operations in which heat and mass transfer rates are matched to those required by the process. This ideology can more easily be achieved by converting batch processes to continuous processes such that small elements of fluid can be continuously exposed to the required hydrodynamic and thermal environments.

It has been known for a long time that fatty acid alkyl esters can be produced from either the base catalyzed transesterification or acid catalyzed esterification of a triglyceride with an alcohol. It is interesting that the process has been extensively used during periods of war as a source of the co-product, glycerol, which was used for the production of explosives. However, it is the long chained ester which is now receiving the attention as it is a potential fuel which can offset a significant fraction of the current demand of diesel fuel. Many natural plant sources of triglycerides exist, including but not limited to soy, canola, palm and cotton seed oils. Animal derived oils, such as but not limited to, beef tallow and fish oil have also been found to be acceptable sources. Commonly, methanol is used in the production producing a Fatty Acid Methyl Ester (FAME) which is often referred to as biodiesel. If other alcohols are used the alkyl ending of the chain (and name) takes that of the alcohol used. In the reaction the triglyceride molecule is fragmented into three smaller FAME molecules and one glycerol molecule. The process overcomes many of the problems associated with attempts to utilize the triglycerides directly, which predominately result from difficult atomization, due to the high viscosity and poor vaporization and combustion characteristics. The reaction reduces the viscosity of the oil by close to an order of magnitude (depending on feedstock) and results in a fuel with similar physical characteristics and energy density as conventional number two fuel. It has also been extensively shown that significant emissions are reduced through the combustion of neat biodiesel or biodiesel blends. This is attributed to the partially oxygenated nature of the molecule which vastly reduces the probability of any products leaving the combustion zone in any other form other than the products of complete combustion.

Biodiesel has been traditionally produced using batch reactor technology. Typically the oil is preheated and fed into the reaction vessel. The alcohol and catalyst are mixed and also added to the reaction vessel. The vessel is often jacketed to minimize heat loss and maintain reaction temperature. The process is often conducted at temperatures around 150° F. A reflux condenser is often used to prevent pressurization of the system and capture any alcohol vapors. An internal impeller is often used to provide shear to extend the contact between the two phases. If the same vessel is to be used as a decantation vessel to separate the heavier glycerin phase from the biodiesel phase this stirring is sometimes reduced or stopped towards the end of the reaction to prevent further breakup and size reduction of the glycerin droplets. Sometimes an external device such as centrifuge is used to perform this separation.

Biodiesel production based on batch technology suffers from many drawbacks and limitations. Firstly it is well known that the kinetic rate of the transesterification reaction is considerable at the temperatures typically used in the batch reactor. However, mass transfer is so limited by the poor hydrodynamic environment created by a single impeller that the process exhibits a large induction period. This induction period is primarily attributable to poor mixing between the immiscible oil and alcohol phases. Even after the passing of this induction period the time conversion profile does not approach that dictated by the kinetics of the process. A batch process typically allows two hours for the reaction to proceed to equilibrium; however, if mass transfer limitation were removed the process can be completed within minutes. This time saving allows vastly different reactive systems to be designed which allow rapid rates of reaction to be achieved as well as resulting in high final conversions.

In the case where the same reaction vessel is used as the decantation vessel then the time for settling will be very long. Typically reaction vessel has a height to diameter ratio greater than 1. Thus a glycerin droplet at the very top of the vessel has a considerable distance to fall before it arrives at the biodiesel glycerin interface. Assuming negligible convective or thermal currents exists and based on an average drop size then Stoke's Law can be used to estimate the average drop velocity and hence the time for settling. If a secondary continuous separation device is utilized, such as a centrifuge, than overall turn around time of the process may be reduced. This is generally only true if a relatively large device is used such that it can process the entire contents of the reactor faster than the contents would naturally settle. Thus, for this technique to be desirable large continuous devices must be utilized. Due to the financial as well as maintenance issues attached with such a technique this is not deemed to be a desirable solution.

Some processes utilize two batch reactors in series in a continuous manner. Utilizing a batch reactor in this manner is often referred to as a Continuously Stirred Tank Reactor (CSTR). In the process a CSTR is continuously fed with a preheated mixture of oil, alcohol and catalyst. Simultaneously product is continuously removed from the same vessel at the same rate as the feed. The size of the vessel is calculated to give sufficient average residence time in the vessel for the process to proceed to the desired point. The product of the first CSTR is directed to a separation device where the biodiesel and glycerin are separated. The partially reacted biodiesel mixture is then fed into a second CSTR, along with more catalyst and alcohol, where the second stage occurs. Again product is continuously removed and the glycerin separated. The second vessel is sized such that the conversion of the outlet stream is that required from the process.

The above process can be broadly described as a continuous process but still suffers from the same mass transfer limitation inherent in the batch system. It is well known that the outlet composition of a CSTR is the same as the average composition within the vessel. This effect reduces the driving force of the process resulting in slower kinetics. These two factors result in systems with extremely large holdup times which greatly complicates startup and shut down and serious process and safety issues must be addressed. Also, the conversion in the second CSTR can never achieve equilibrium as fresh feed is always being mixed into the system. Thus such a system can never achieve really high conversion and this may impose significant future implications if currently legislation regarding biodiesel were to change.

There exists a number of U.S. patents directed to biodiesel fuels including U.S. Pat. No. 6,015,440 issued to Noureddini. Triglycerides are reacted in a liquid phase reaction with methanol and a homogeneous basic catalyst. The reaction yields a spatially separated two phase result with an upper located non-polar phase consisting principally of non-polar methyl esters and a lower located phase consisting principally of glycerol and residual methyl esters. The glycerol phase is passed through a strong cationic ion exchanger to remove anions, resulting in a neutral product which is flashed to remove methanol and which is reacted with isobutylene in the presence of a strong acid catalyst to produce glycerol ethers. The glycerol ethers are then added back to the upper located methyl ethyl ester phase to provide a biodiesel fuel. Noureddini teaches an apparatus that includes a centrifuge; however, Noureddini does not teach an intensified process for the production of biofuel.

U.S. patent application No. 2003/0175182 applied for by Teall et al. describes a process for the small scale production of biodiesel. The process can be described by the steps of mixing, reaction, separation, distillation and filtration. The alkaline catalyst is dissolved in a low order alcohol and is co-fed with the triglyceride to the reaction vessel. An external stream is removed from the reaction vessel and passed through an array of centrifuges where glycerin is separated from the biodiesel. The biodiesel is returned to the reaction vessel. The glycerin stream enters a distillation column where the excessive methanol is recovered and recirculated to the reaction vessel. Teall teaches of a process to produce biofuels; however, Teall does not teach of a modular process capable of high throughput in which each unit operation is optimized through the use of process intensification.

U.S. patent application No. 2006/0021277 applied for by Petersen et al. describes a continuous process for the production of biodiesel. The process consists of two Continuously Stirred Tank Reactors (CSTRs) each with an external settling tank, arranged in series. The first CSTR is continuously fed with preheated triglyceride, catalyst and alcohol. Partial reaction occurs within the vessel. At the same rate as the feed is added to the CSTR a product stream is removed and is directed to a gravity separation tank. Here the glycerin gravity separates from the biodiesel to form a dense layer at the bottom of the tank. Through careful choice of exit pipes arrangements the tank has a self controlling mechanism to maintain the interface at the desired set point. The biodiesel over flow is directed to the second CSTR where the process is repeated. The two volumes of the tank and overall residence time in the process is large, hence, Petersen does to teach of a process exhibiting optimized kinetics resulting in a small process fluid inventory.

U.S. Pat. No. 6,364,917 issued to Matsumura et al. teaches a process for producing a fuel from plant oil. Matsumura teaches a method of heating the oil, mixing the oil with water and/or ozone, and agitating the mixture of oil and water and/or dissipating the ozone. The oil is then separated from the water. Matsumura further teaches equipment for producing the fuel including an agitator tank and an optional, separate centrifuge. Matsumura does not teach a process with minimized footprint.

U.S. Pat. No. 6,712,867 to Boocock discloses a process for the esterification of a triglyceride. The process comprises forming a single phase solution of a triglyceride in an alcohol selected from methanol and ethanol. The solution further comprises a co-solvent in an amount to effect formation the single phase and a base catalyst for the esterification reaction. After a period of time, ester is recovered from the solution. The esters may be used as biofuel or biodiesel. The process may be optionally operated in a batch or continuous process. However, Boocock does address the issues relating to the optimization of heat and mass transfer issues throughout the process.

U.S. Pat. No. 5,908,946 to Stern et al. discloses a process for the production of linear monocarboxylic acid esters with 6 to 26 carbon atoms. Vegetable oils or animal oils are reacted with monoalcohols having a low molecular weight, for example 1 to 5 carbon atoms, in the presence of a catalyst that is selected from among zinc oxide, mixtures of zinc oxide and aluminum oxide, and the zinc aluminates that correspond to the formula: $ZnAl_2O_4$, x ZnO, y $Al_2O_3$ (with x and y each being in the range of 0-2) and having more particularly a spinel type structure of an ester that can be used as a fuel or combustible and a pure glycerine. The process may optionally be operated in a continuous process that includes several autoclaves and decanters. Thus, Stern does not teach of an intensified process for the continuous production of biodiesel fuel.

SUMMARY OF THE INVENTION

One feature of the present invention relates to an intensified chemical process for the production of biodiesel which has a smaller footprint and is substantially cheaper to produce than traditional batch technology.

Another feature of the present invention relates to a process which allows for the production of biodiesel on a scale of 1 to 80 million liters per year per process.

Another feature of the present invention relates to a process in which higher throughputs are obtained through replication or base process.

Another feature of the present invention relates to a process which allows for the production of biodiesel in a highly energy efficient manner.

Another feature of the present invention relates to a process which the biodiesel produced surpasses the requirements of the ASTM standards.

Another feature of the present invention relates to a process which allows the conversion of an oil which contains an appreciable content of free fatty acids to produce a methyl ester product in high yields.

The present invention comprises, in one exemplary embodiment, a biodiesel production process comprising intensified processing modules. Each unit operation in the process is optimized to minimize any impedance resulting from heat and mass transfer limitations. The resulting process design is substantially smaller, lighter and cheaper to produce than conventional batch technology. The small footprint of the process and high throughput capabilities allow the system to be transported preconstructed to its point of use.

Other features and advantages of the present invention will become apparent upon reading the following detailed description of embodiments of the invention, when taken in conjunction with the appended claims.

BRIEF DESCRIPTION OF THE DRAWINGS

The invention is illustrated in the drawings in which like reference characters designate the same or similar parts throughout the figures of which.

The examples set out herein illustrate several exemplary embodiments of the invention but should not be construed as limiting the scope of the invention in any manner.

DETAILED DESCRIPTION OF THE PREFERRED EMBODIMENTS

Figure 1:
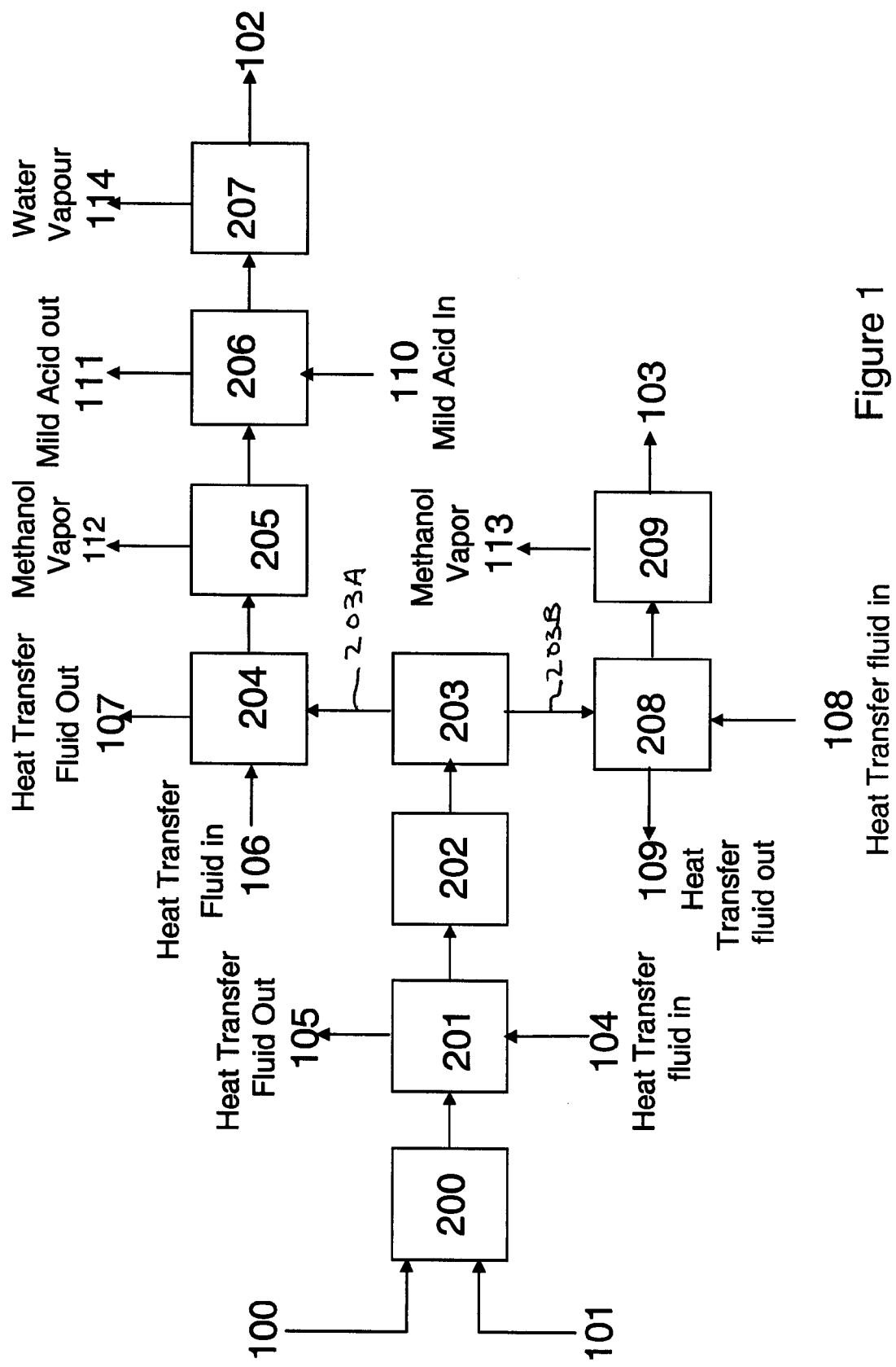
FIG. 1 is a schematic block diagram of one exemplary embodiment of a process of the present invention.

A schematic block diagram of one exemplary embodiment of the process of the present invention, highlighting the important flow paths, is shown in FIG. 1. A brief overview is given followed by a more detailed description of each unit operation describing how it contributes to plant size reduction. Only the key components of the system are highlighted here. It is possible to include more steps both before and after the key conversions steps described below. For example if an oil with a large water content was to be processed it would be possible to dry the oil prior to the oil entering the process described below. If a thermal process, for example a flash or stripper, was used, it would be possible to feed the oil preheated into the steps below to minimize energy requirements.

Oil, composed primarily of triglycerides (100) along with a stream containing a lower order alcohol containing a suitable quantity of dissolved catalyst (101) enters the homogenizer (200) preferably an inline homogenizer. The two phases are exposed to extreme shearing force, within the homogenization device, to extend the area of contact. Often the homogenization device will utilize a workhead consisting of a rotor and stator, although other methods may be used to form the emulsion. The emulsified mixture exits the homogenizer (200) and enters a heat exchanger (201). Here heat is transferred to the emulsion to until the required reaction temperature is achieved. The heated emulsion exits the heat exchanger (201) and enters a reaction chamber (202). The reaction chamber (202) has sufficient internal volume to ensure the fluid is held up for the required extent of reaction to occur. The reaction chamber (202) is also sized to produce a hydrodynamic environment to promote the reaction. Upon exiting the reaction chamber (202) the mixture is quenched prior to entering a gravity driven separation device (203), which promotes the heavier glycerin phase to separate from the biodiesel and form a discrete layer at the bottom. Two streams exit the separator (203).

The first stream, which is biodiesel rich, exits the separator (203) at arrow 203A and enters a booster heat exchanger (204). Here the temperature of the stream is increased while the mixture is held under pressure. The superheated mixture exits the booster heat exchanger (204) and is sprayed using a conventional nozzle into the stripper (205). The stripper is evacuated and held under a sufficient vacuum such that the majority of the residual methanol or other volatiles readily undergo vaporization. The gaseous phase exit the stripper through the vapor outlet (112) and are cooled and liquefied in the condenser. The biodiesel exits the stripper (205) and enters an aqueous contactor (206). A dilute acid such as, but not limited to sulphuric or citric acid (110) may be used. Water soluble components are preferentially extracted into the water phase and exits as water vapor at (114). The biodiesel exits the contactor (206) and enters a drier (207) prior to being sent to fuel storage container (102).

The second stream, which is glycerin rich, exits the separator (203) at arrow 203B and enters the booster heat exchanger (208). The mixture is held under pressure while heat is applied (108). Here the temperature of the stream is increased while the mixture is held under pressure. The superheated mixture exits the booster heat exchanger (208) and is sprayed into the stripper tank (209). Any residual methanol or other volatiles are vaporized and exit the unit through the volatiles exit (113). The glycerin rich stream exits stripper tank (209) where it may be directed to storage (103) or for further workup via a stream.

The homogenization step (200) is one of the most important unit operations for the production of biodiesel. If the alcohol and triglycerides are not sufficiently contacted then a significant induction period will occur. Poor mixing is one of the reasons why batch processes often require two hours or more to achieve equilibrium conversion. In the present invention an inline homogenizer is preferably used to exert high levels of lateral shear upon the two phases. This operation results in extensive disintegration of the methanol phase producing droplets in the micron range. The emulsion is sufficient stable such that even at room temperature phase separation does not occur prior to extensive reaction. The mixing is sufficient such that further downstream mixings are not required. Operating in the downstream unit operations without any further mixing allows the glycerin droplets to begin ripening as soon as they are formed which aids in phase separation.

The alcohol and catalyst stream (101) can be produced a number of ways. In a first exemplary method the catalyst is in the form of a concentrated sodium or potassium methylate salts dissolved in methanol. The solution may contain 25-30% (by weight) of the salt with the excess being methanol[2]. In this case the catalyst stream is mixed with further methanol to give a stream of the correct composition and flow to form the stream (101). In a second exemplary method two tanks are operated in a semi-batch manner. One tank is used to supply the process while the second tank prepares the catalyst mix. Sodium or potassium hydroxide[2] or is added to a given amount of methanol and the two components are readily mixed in the tank. When the first tank runs low the second tank is brought on line. Here the first tank is refilled with the appropriate amount of a catalyst and methanol and the process is repeated. In a third exemplary method, inline disintegrators may be used to produce the catalyst stream. Here a small amount of solid catalyst (sodium hydroxide or sodium methylate) is continuously added and dissolved in the methanol stream. The addition mechanism acts to disintegrate the catalyst into a small particle size to aid in the dissolution step. Further catalysts, including but not limited to potassium hydroxide and potassium methylate, have also be found suitable for this process.

The process of the present invention allows the equilibrium, or near equilibrium, conversion between the triglyceride and alcohol phase to be achieved in a rapid and efficient manner. However, final conversion level is closely related to the ratio of triglyceride to methanol introduced into the front end of the process. The time to achieve this equilibrium conversion is also related to the concentration of catalyst introduced into the front end of the process. It is thus imperative that an accurate method is utilized to ensure that the desired stoichiometry is achieved. It has been found that the use of Coriolis mass flow controllers work sufficiently well for this application. It should be noted that other techniques which accurately meter either mass of volumetric flows known to those skilled in the art may be used in this process.

After the two phases are emulsified they enter a heat exchanger (201), preferably a plate heat exchanger, to bring the mixture up to the reaction temperature. There are a number of commercial suppliers of such units. A plate heat exchanger utilizes a number of alternate parallel channels separated by a thin plate. Process fluid flows in one set and heat transfer fluid in the second. Due to the high rates of heat transfer the units are typically much smaller than a shell and tube counterpart. Utilizing small heat exchanger aids in the design of an intensified plant with a small footprint. The heat transfer fluid inlet stream (104) is typically arranged to be in a counter current flow regime with the process fluid. Common heat transfer fluids include, but are not limited to, water, pressurized water, oil, heat transfer fluids and steam. A temperature transducer contacts the process fluid exiting the heat exchanger and is used to control the rate of heat transfer in the unit. The transesterification reaction proceeds at almost all temperatures but a compromise between reaction time and yield loss due to soap formation has to be made. It has been found that the present invention operates particularly well in the range of about 80-95° C., with particularly favorable results being gained while operating in the range of about 85-90° C.

The reaction chamber (202) is sized to provide sufficient hold-up volume for the reaction to proceed to the required point. For example, for an annual production rate of 19,000,000 liters this equates to a volume of about 360 liters, which provides a reaction period of six minutes. These figures assume that the process has an up time of about 80%. The reaction chamber (202) is insulated to prevent significant heat loss. As the reaction is relatively unenergetic heat neither has to be supplied or removed from the process.

In a preferred embodiment the reactor (202) consists of a tubular reactor designed such that the flow preferably operates with a Reynolds Number greater than about 2,100 and with a length to diameter ratio greater than about 300.

If an oil is being processed which contains free fatty acids, soap may be formed due to the reaction between the alkaline catalyst and free fatty acid. The soap formed can act as a surfactant and result in excessive amounts of biodiesel being entrained into the glycerine phase. The present invention can minimize this yield loss by subjecting the reaction mixture to high levels of shear only at the point of homogenization. At this point soap is formed but the product of the reaction, biodiesel and methyl ester, are not present. For the soap to act as a surfactant and to form micelles requires further mixing after of during the production of the reaction products. However in the present invention the hydrodynamic environment produced by the flow through the reactor is not sufficiently turbulent to allow this phenomena to occur to an appreciable level. The result is that oils containing high levels of free fatty acids can be directly processed while achieving high yields of biodiesel.

The flow exiting the reaction chamber (202) consists of biodiesel, glycerin, excess methanol, catalyst and small amounts of unreacted tri, -di- and mono-glycerides. The next operation is designed to separate the glycerin co-product from the biodiesel. It is noteworthy that due to three hydroxyl groups the glycerin is much more hydrophilic than the biodiesel. This effect results in strong partitions of the other components between the two phases with the polar components preferentially portioning into the glycerine phase and nonpolar components portioning into the biodiesel phase. The majority of the catalyst and any soap present as well as approximately half of the excess methanol exit with the glycerin. The glycerin phase is denser than the biodiesel phase and readily accumulates at the bottom of gravity separation devices. The separation mechanism is initiated by very small droplets of glycerin agglomerating into larger droplets. This process of agglomeration is known as ripening. The bigger the droplet becomes the faster it travels downwards. In the present invention the separation can occur in a decantation tank or in a decantation tank with a coalescing packing which promotes ripening and thus enhances separation. In the biodiesel industry it is common to use centrifuges to perform this operation. Centrifuges create large artificially gravity forces which rapidly increase the velocity that a droplet travels. Indeed, a centrifuge can be used in the current arrangement as they are relatively small and operate in a continuous manner. However such units are often unreliable and can be rather expensive.

In a preferred embodiment of the present invention a tank with a sufficient volume to provide about 3 hours of hold up time and with a length-to-diameter ratio in the range of about 1:4 to about 1:10 has been found to provide satisfactory separation, more preferably in the range of about 1:4 to about 1:5. The tank may also include baffles to promote plug flow behavior and prevent thermally driven short circuiting to occur.

Alternatively, a packed coalescing tank is used as the separator (203) to separate the glycerin phase from the biodiesel phase. The packing is preferably chosen to be hydrophilic such that the glycerin droplets are attracted to the packing. By the glycerin droplets preferentially accumulation on the packing the probability of agglomeration and ripening is greatly enhanced and hence the process happens much quicker. Through the use of coalescing packing the volume of the unit is much reduced and approaches the footprint used by a centrifuge. Particularly satisfactory results have been found using fiberglass and steel and Teflon and steel combinations. The separator was found to be capable of separation efficiency greater than about 99%.

The glycerine rich stream, exiting the second exit (203B) from the separation device (203) may contain appreciable amounts of soap. In some applications it may be desirable to add small volumes of acid (at 110) to this mixture to back crack the soap into free fatty acids. This technique allows the recovery of the free fatty acids after the flash and results in a higher purity glycerine. This technique also minimizes the formation of foam within the flash vessel. It is also acceptable to back crack any soap after the flash stage, again through the addition of an acid. Anhydrous sulphuric acid has been found to be an acceptable reagent.

The glycerin rich stream (203B) enters a booster heat exchanger (208). The heat transfer fluid (108) is sufficiently hot to bring the glycerine up to a flash temperature of about 120° C. A plate heat exchanger similar to (201) may be used for this operation.

The glycerine stream passes through a back pressure controller and is sprayed into a packed stripper tank (209) which is held under vacuum. The packing is used to create a thin film to increase the mass transfer coefficient and hence expedite the removal of methanol from the glycerine. The methanol exits the stripper tank (209) via the solvent exit line (113). A number of packings are suitable; 2.5 cm Rashig (available from suppliers such as Jaeger Products, Houston, Tex.) has given particularly acceptable results. It is also possible to spray the fluid directly onto the wall of the stripper tank (209) vessel to create the thin film. The glycerin exits the stripper tank (209) where it may go (103) to optional further work up, possibly including, neutralization and removal of the catalyst and the back cracking of any soap. Once the soap is back cracked it readily separates from the glycerine to produce a new upper phase.

In some circumstances it may be desirable to recycle a portion of the glycerine exiting the flash back to the inlet side. This technique can be used to further enhance the methanol recovery efficiency.

The biodiesel rich stream, exiting from the upper exit of the separation device (203) may contain trace quantities of catalyst. This catalyst can be neutralized by the addition of a suitable acid (110). The neutralization of the catalyst minimizes any reverse reaction occurring during methanol recovery. Anhydrous sulphuric acid has been found to be an acceptable reagent.

The biodiesel rich stream enters a booster heat exchanger (204). The heat transfer fluid (106) is sufficiently hot to bring the biodiesel up to a flash temperature of about 120° C. A plate heat exchanger similar to (201) is used for this operation.

The biodiesel stream passes through a back pressure controller and is sprayed into a packed stripper tank (205) which is held under vacuum. The packing is used to create a thin film to increase the mass transfer coefficient and hence expedite the removal of methanol from the biodiesel. The methanol exits the tank (205) via the solvent exit line (112). The solvent is condensed in a plate heat exchanger (201) operating with chilled water. The methanol is captured (113) and stored for reuse. A number of packings are suitable for the stripper, however 2.5 cm Rashig rings have given particularly acceptable results. It is also possible to spray the fluid directly onto the wall of the stripper vessel to create the thin film.

The aqueous contactor (206) is used to contact the biodiesel and a water or mild acid stream (110) to allow water soluble components to partition into the aqueous phase. The water soluble components may include trace amounts of soap, catalyst and methanol. For this solution a counter current wash column has proved to be very satisfactory. The counter current column is packed with 2.5 cm Rashig rings to promote contact between the two phases. For example, for a 19,000,000 liter per year rate of production of biodiesel the column is about 0.6 m in diameter. Biodiesel enters through a jut situated about 30 cm above the bottom of the column with water or mild acid entering through a jet; about 30 cm below the top of the column. Density differences cause the water to drop and biodiesel to rise through the packing. Here mass transfer occurs and the biodiesel is purified. The column operates in a countercurrent manner such that multiple theoretical stages are possible in one column. This results in both minimal water consumption and a more pure biodiesel. A column of about 5.4 m in height has minimal footprint and can approach four theoretical contact stages. Density loops are arranged at the top and bottom such that the average interface level between the water and biodiesel can be controlled and both components exit the system without the use of any pumping mechanism.

The biodiesel then enters a packed drier (207) which is held under $9*10^4$ Pa of vacuum. The biodiesel is sprayed into the top of the drier and flows down the packing in the form of a thin film. Any water dissolved in the biodiesel is readily atomized and exits the unit via the water vapor outlet (114). The biodiesel is then directed to product storage container (102).

The present invention relates to an intensified biodiesel process. To illustrate how the results of the design process a 1,900,000 liters per year process has a footprint less than 60 square meters. This figure is substantially smaller than a biodiesel process based on batch technology.

In a preferred embodiment of the present invention the entire apparatus is mounted on four skids or other base plate and connected together. The four skids each contain the equipment to perform a part of the overall process. The four stages can be subdivided in a number of ways, a preferred way being, reaction, separation, methanol recovery and water contactor. The smaller skids allow easy transportation of the entire plant, preconstructed, to the point of use. The process is energy efficient, safer due to lower process inventories and more economic than current technology.

The invention will be further described in connection with the following examples, which are set forth for purposes of illustration only. Parts and percentages appearing in such examples are by weight unless otherwise stipulated

EXAMPLES

Example 1

Figure 2:
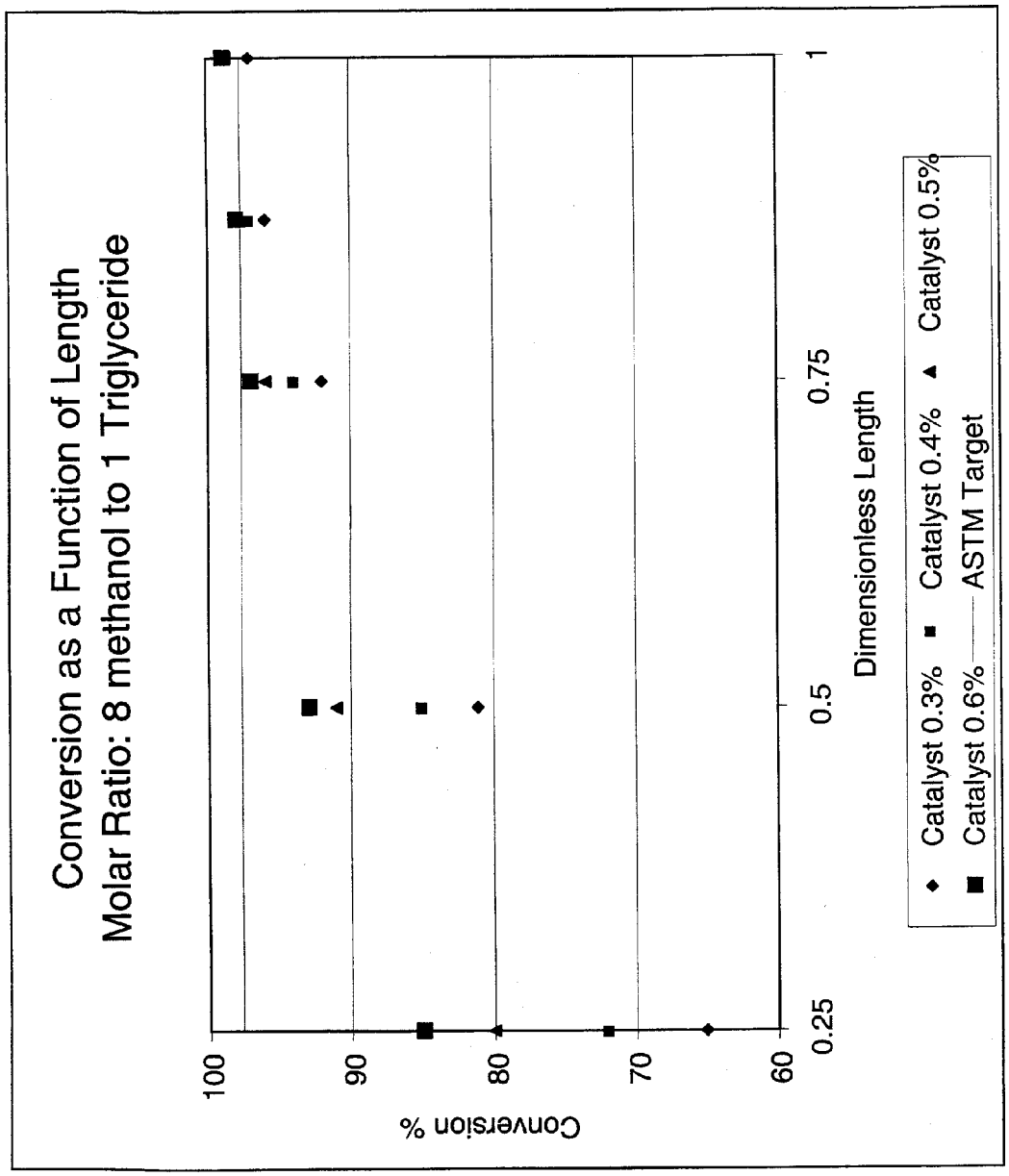
FIG. 2 is a graphical representation of triglyceride conversion profiles along the length of the reactor.

Oil, methanol and sodium hydroxide catalyst were continuously fed into a channel reactor. The rates chosen gave a molar ratio of eight mols methanol to 1 mol triglyceride. The methanol contained the catalyst (sodium hydroxide), the mass of which was in the range 0.3 to 0.6% by weight of the oil. The length of the reactor provided up to six minutes residence time. The mixture was passed through a Silverson inline homogenizer in which a stable microemulsion was formed. The mixture was then heated to a temperature of 90° C. in a plate heat exchanger. The mixture flowed through the channel reactor where reaction occurred. Samples were withdrawn at various lengths down the reactor and analyzed for methyl ester content. It was found that both increasing length and increasing catalyst loading. The conversion obtained, as a function of length, can be seen in FIG. 2. The conversion levels required by the ASTM 6751 could be achieved with a catalyst loading greater than 0.4%.

Example 2

An apparatus was constructed consisting of four skids. Skid #1 was a reaction skid of overall dimensions 1.5 m wide, 4.5 m long with a maximum height of 1.8 m. 45.6 liters per minute of refined soy oil, 12 liters of anhydrous methanol and 0.75 kg per minute of 30% sodium methylate in methanol solution were fed onto the reaction skid. The mixture was homogenized and heated to 90° C. prior to flowing into the 7.5 cm ID reactor which has sufficient length to provide six minutes of residence time. The fluid exited the first skid and flowed onto the second skid. Skid #2 had a dimension 1.8 m by 7 m and 1.8 m high. The skid contained an 11,400 liter tank of dimensions 1.65 m diameter and 6.6 m long. The tank provided a hold up of approximately 3 hours. In this tank a glycerin-rich phase formed in the lower portion of the tank. The biodiesel rich stream exited from an upper port and flows onto skid #3. Skid #3 had overall dimensions 2.4 m wide, 4.5 m long and 4.2 m high. The biodiesel stream was heated to 120° C. while being held under a pressure of 0.8 MPa. The stream was sprayed into an evacuated packed tank such that any methanol present was vaporized. The biodiesel stream exited skid #3 and flows onto skid #4. Skid #4 had overall dimensions of 1.5 m wide, 4.2 m long and 4.8 m high. The biodiesel entered the bottom of a 4.8 m high, 0.6 m diameter packed counter current wash column. Acidified water entered the top of the column. The biodiesel rose through the column while the water phase dropped. Water soluble impurities were extracted from the biodiesel stream. The washed biodiesel passed through a vacuum drier prior to being sent for storage. Samples of the biodiesel were sent for analysis and were found to pass all of the requirements described in ASTM 6751. The apparatus and process described here was capable of producing about 19,000,000 liters of biodiesel per year. The skids can be arranged to occupy a total footprint of less than 5 m by 12 m. The apparatus utilized less than 25 kW of electrical power and 40 liters per hour of number 2 fuel oil to operate.

The text here is used to described to the attributes of the process which have been intensified resulting in the smaller footprint. Ancillary equipment such as pumps etc are also used in the process. Further unit operations, both upstream and down stream, can be utilized but are not included here to improve clarity of the invention. These may include a front end esterification process such that fatty acids are converted to biodiesel prior to feeding into the plant. Downstream unit operations may include glycerine purification, biodiesel filtration or the addition to flow modifiers or gel point modifiers to the biodiesel stream.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. It should further be noted that any patents, applications and publications referred to herein are incorporated by reference in their entirety.

What is claimed is:

1. A method for continuous production of biodiesel, comprising:
    charging a homogenization device with a quantity of an oil as a nonaqueous phase, a quantity of a lower order alcohol as an aqueous phase, and a quantity of a catalyst;
    exposing the aqueous phase and the nonaqueous phase to a shearing force within said homogenization device to form an emulsified mixture;
    transferring said emulsified mixture to a heat exchanger device;
    heating said emulsified mixture until a reaction temperature is reached;
    transferring said heated emulsified mixture to a reaction chamber containing a hydrodynamic environment so that a chemical reaction occurs producing a first reaction product;
    quenching said first reaction product;
    transferring said first reaction product to a gravity driven separation device; and,
    activating said separation device so as to form a heavier glycerin phase and a biodiesel phase.

2. The method of claim 1, further comprising:
    transferring said biodiesel phase to a booster heat exchanger device;
    heating said heat exchanger device and said biodiesel phase under pressure;
    spraying said biodiesel phase into a stripper device;
    applying a vacuum to said stripper device such that the majority of any residual methanol and other volatile components are vaporized;
    condensing and liquefying said gaseous phase in a condenser to form a liquid phase;
    contacting said liquid phase with an acid;
    extracting water soluble components into a water phase and removing as water vapor; and,
    removing remaining said biodiesel and drying said biodiesel.

3. The method of claim 1, further comprising;
    transferring said glycerin phase to a booster heat exchanger;
    heating said glycerin phase under pressure;
    spraying said heated glycerin phase into a stripper device such that any residual methanol and other volatile components are vaporized; and,
    transferring said glycerin to a storage container.

4. The method of claim 1, wherein said acid is selected from the group consisting of sulfuring acid and citric acid.

5. The method of claim 1, wherein said catalyst is selected from the group consisting of sodium methylate salt, potassium methylate salt, sodium hydroxide and potassium hydroxide.

6. The method of claim 1, wherein said separator is a packed coalescing tank.

* * * * *